United States Patent [19]
Burack et al.

[11] Patent Number: 5,208,892
[45] Date of Patent: May 4, 1993

[54] TRIAZINE OPTICAL WAVEGUIDES

[75] Inventors: John J. Burack, Toms River; Treliant Fang, Lawrenceville; Jane D. LeGrange, Princeton, all of N.J.; Jose A. Ors, New Hope, Pa.

[73] Assignee: AT&T Bell Laboratories, Murray Hill, N.J.

[21] Appl. No.: 859,758

[22] Filed: Mar. 30, 1992

Related U.S. Application Data

[60] Division of Ser. No. 797,632, Nov. 25, 1991, which is a continuation-in-part of Ser. No. 748,375, Aug. 22, 1991, abandoned, which is a continuation-in-part of Ser. No. 525,947, May 18, 1990, Pat. No. 5,045,364.

[51] Int. Cl.$^5$ .............................................. G02B 6/10
[52] U.S. Cl. .................................. 385/129; 385/143; 427/162
[58] Field of Search ............... 385/129, 130, 142, 143, 385/16; 156/643; 427/162, 346, 385.5, 404, 407.1, 261, 270

[56] References Cited

U.S. PATENT DOCUMENTS

| 4,511,209 | 4/1985 | Skutnik | 385/129 X |
| 4,715,672 | 12/1987 | Duguay et al. | 385/129 |
| 5,011,623 | 4/1991 | Yoshinaga et al. | 385/122 X |
| 5,045,364 | 9/1991 | Fang | 385/16 X |

OTHER PUBLICATIONS

"Evaluating Polyimides as Lightguide Materials," by R. Reuter et al., *Applied Optics*, vol. 27, No. 21, Nov. 1, 1988, pp. 4565-4570.

*Primary Examiner*—John D. Lee
*Assistant Examiner*—Phan T. Heartney
*Attorney, Agent, or Firm*—R. B. Anderson

[57] ABSTRACT

An optical waveguide (11) is composed substantially entirely of triazine.

2 Claims, 1 Drawing Sheet

TRIAZINE OPTICAL WAVEGUIDES

This is a division of application Ser. No. 07/797,632 filed Nov. 25, 1991. Application Ser. No. 07/797,632 filed Nov. 25, 1991 is a Continuation-In-Part of Ser. No. 07/748,375, now abandoned, which in turn is a Continuation-In-Part of the patent application of T. Fang, Ser. No. 07/525,947 filed May 18, 1990, now U.S. Pat. No. 5,045,364 granted Sep. 3, 1991 which is hereby incorporated herein by reference.

TECHNICAL FIELD

This invention relates to polymer optical waveguides.

BACKGROUND OF THE INVENTION

The publication, "Evaluating Polyimides as Lightguide Materials," by R. Reuter et al., *Applied Optics*, Vol. 27, No. 21, Nov. 1, 1988, pp. 4565–4570, describes the use of a number of different polymers as media for transmitting lightwaves. Various polymer materials such as polymethyl methacrylate and various polyimides have been proposed as materials from which lightguide or optical waveguide patterns can be made on a flat substrate. Such films may be only a few microns in thickness and can be used to transmit light to optoelectronic devices on a substrate much the way printed circuits transmit electrical current on a printed wiring board. Effective transmission requires that the optical waveguide material have a relatively low attenuation or loss with respect to the light beam transmitted and that it have a higher optical index of refraction than the surrounding media. The materials mentioned in the paper have a sufficiently high index of refraction and a sufficiently low loss, at least at certain optical frequencies, to be useful as practical media for optical waveguide purposes.

The article points out that a major disadvantage of polymethyl methacrylate is its poor thermal and environmental stability. Disadvantages of polyimides include their high cure temperature, typically above three hundred degrees Centigrade, which could be damaging to certain substrates such as printed wiring boards made of commonly used resin materials, and their relatively high cost.

There is therefore a continued long-felt need for polymer waveguides that can transmit light with low loss and high efficiency, that have good thermal and environmental stability, can be made without subjecting them to inordinately high cure temperatures, are of low cost, and are amenable to mass production.

SUMMARY OF THE INVENTION

In accordance with the invention, we have found that practical optical waveguides may be made of triazine polymers (also known as polycyanate resins). Such waveguides do not require excessively high temperatures in their fabrication, are of lower cost than polyimides, have high temperature and environmental stability, and can be efficiently manufactured in printed circuit form.

These and other objects, features, advantages of the invention will be better understood from a consideration of the following detailed description taken in conjunction with the accompanying drawing.

DETAILED DESCRIPTION

Figure 1:
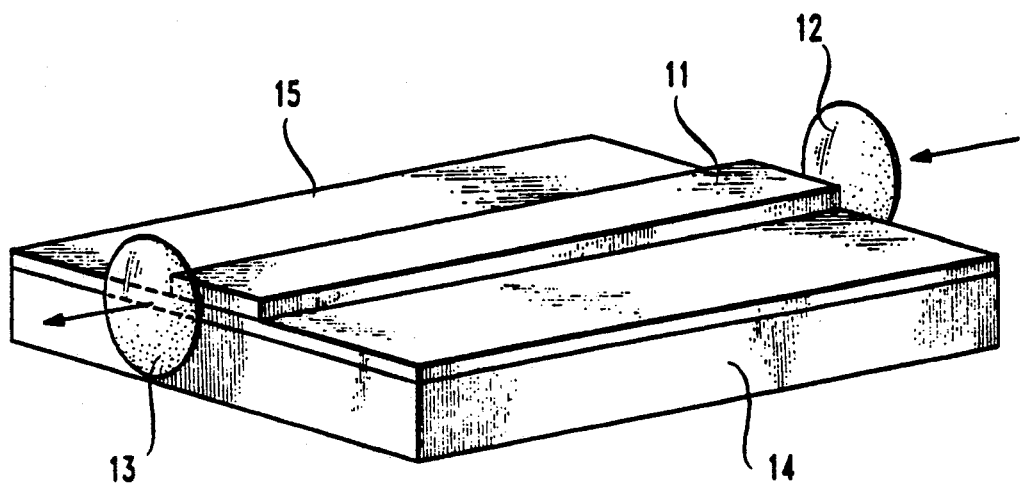
FIG. 1 is a schematic perspective view of an optical waveguide in accordance with an illustrative embodiment of the invention.

Referring now to FIG. 1, there is shown schematically an optical waveguide 11 used for propagating light from one end thereof to the other, as shown by the arrows. Lenses 12 and 13 are typically used to apply light to and remove light from the waveguide 11. In accordance with the invention, the waveguide 11 is substantially completely composed of cured triazine. The waveguide 11 is supported on a substrate 14 upon which is formed a layer 15 of low refractive index material. The two primary requirements for an optical waveguide is that it must have a higher refractive index than the surrounding media and it must have a low attenuation or loss with respect to the transmitted light. Triazine has a typical refractive index of approximately 1.6, which is sufficiently high to be higher than any of various materials that could be used as a cladding. For the experimental use shown, the "cladding" on three sides of the waveguide is air which has a refractive index of 1.0. The layer 15 may be of glass which has a much lower refractive index than triazine. It is to be noted that in commerically useful devices, the waveguide 11 would typically be used to transmit light to and from any of various optoelectronic devices or passive components such as couplers; these various known uses for optical waveguides have not been illustrated in the interest of brevity and simplicity. The waveguide itself can constitute a passive device such as a coupler, a power combiner, or a power divider, as is known.

Figure 2:
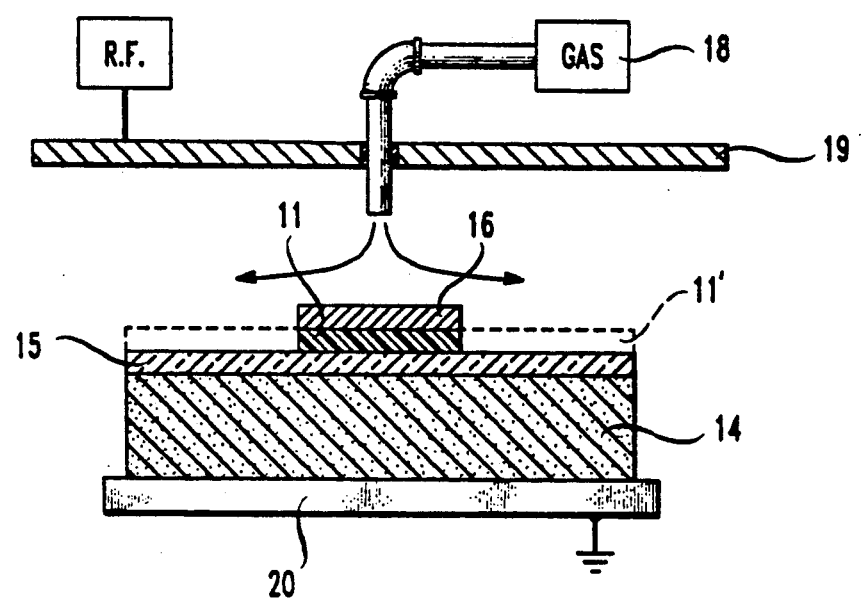
FIG. 2 is a schematic view of apparatus that may be used for making the device of FIG. 1.

An advantage of using triazine as a waveguiding material is that waveguide circuits of triazine can be easily and conveniently made and are amenable to mass production. Referring to FIG. 2, a waveguide pattern can be made by applying over the entire surface of layer 15 a layer 11' of triazine that may have a typical thickness of two microns. Over this, a layer of aluminum is applied, which is patterned by known photolithographic masking and etching to yield an aluminum mask 16 having a configuration corresponding to that of the desired waveguide pattern. The triazine can then be etched in a standard plasma etch reactor, which is shown schematically in FIG. 2. Gas from a source 18 is directed into the space between electrodes 19 and 20, as shown by the arrows. A radio frequency plasma is then formed between electrodes 19 and 20 which enhances a reaction of the gas with the triazine to etch away the unmasked portion of the layer 11', shown by the dotted lines, thereby to leave an etched layer 11 having a configuration conforming to the desired waveguide pattern.

Waveguides such as waveguide 11 of FIG. 1 have been made using commercially available triazine monomer solutions in methylethylketone. One of the compounds is known as Arocy F-405, which is a fluorinated monomer, and the other is REX-368, which is not fluorinated, both of which are available from Hi-Tek Polymers of Louisville, Ky. The triazine compound was diluted to approximately thirty-five percent solids in polypropylene gycol methyl ether acetate (PGMEA). A surfactant, FC-430, commercially available from the 3M Company of Minneapolis, Minn., was added to a concentration of 0.02 percent by weight to insure even spreading of the solutions on the substrate.

The substrate 14 was a silicon wafer, with layer 15 being of silicon dioxide. To insure good adhesion between the monomer film and the substrate, an adhesion promoter comprising 0.05 weight percent 3-aminopropyltrimethoxysilane, ninety-five weight percent methanol and 4.95 percent water was deposited on the surface of layer 15. The triazine monomer was deposited to a thickness of 2.0 microns by spinning the substrate at two thousand rotations per minute for thirty seconds. Curing was done in a glass tube furnace under a nitrogen purge. The curing steps were as follows:

1. One degree Centigrade per minute ramp to one hundred twenty degrees Centigrade.
2. Dwell at one hundred twenty degrees Centigrade for one hour.
3. Ramp at three degrees Centigrade per minute to two hundred thirty degrees Centigrade.
4. Dwell two hours at two hundred thirty degrees Centigrade.
5. Allow to cool overnight in the furnace under a nitrogen purge.

After the triazine film was cured, aluminum was sputtered to a thickness of approximately two thousand three hundred angstroms using a commercially available sputtering machine. Photoresist was spun over the aluminum, the photoresist was baked dry, and the waveguide pattern was imaged using a commercially available contact printer. The photoresist was developed and the exposed aluminum removed in a standard aluminum acid etch. The films were placed in the reactive ion etcher, as shown schematically in FIG. 2, which was a PlasmaLab model, available from the Plasma Technology Company of Avon, England. The triazine 11' was etched at one hundred watts of power and one hundred millitorr pressure in an atmosphere of twenty percent Freon and eighty percent oxygen. After etching, the remaining photoresist and aluminum was removed from the wafer to yield the structure of FIG. 1.

Both of the triazines that were tested had an optical loss of less than three db per centimeter at an optical transmission wavelength of 632.8 nanometers. The fluorinated triazine had a refractive index of 1.5303 at 632.8 nanometers. The unfluorinated triazine had a refractive index of 1.606 at 632.8 nanometers and 1.588 at 1064 nanometers. The films were capable of withstanding temperatures of approximately three hundred degrees Centigrade, which indicates good thermal stability. As pointed out in the aforementioned Fang patent application, a reason for the inherent thermal and environmental stability of triazine is that it is cross-linked in three dimensions, which is unlike PMMA, a thermoplastic material without cross-linking capability. It is believed that the curing temperature of the triazine can be lowered to be less than two hundred degrees Centigrade if this is needed to prevent damage to the substrate 14 during processing. As mentioned before, certain printed wiring boards have a resin composition which is incapable of withstanding the high temperatures required, for example, for curing polyimide.

The embodiments shown are intended to be merely illustrative of the concepts of the invention. For example, the triazine can be made from a synthesized monomer as described in detail in the aforementioned Fang application. Various other embodiments and modifications may be made by those skilled in the art without departing from the spirit and scope of the invention.

We claim:

1. An optical waveguide for guiding light along a path comprising: an elongated polymer element having first and second ends; said polymer element being substantially surrounded by a medium having a lower index of refraction than the polymer element; said polymer element comprising means for transmitting light between the first and second ends thereof, wherein the improvement is characterized in that:
   said polymer element is substantially entirely composed of triazine.
2. The waveguide of claim 1 wherein:
   the triazine is fluorinated.

* * * * *